United States Patent
Tohyama

(10) Patent No.: US 8,952,140 B2
(45) Date of Patent: Feb. 10, 2015

(54) COMPOUND AMYCOLOSE DERIVATIVE, METHOD FOR PRODUCING THE SAME, AND USE OF THE SAME

(75) Inventor: Shigehiro Tohyama, Tokyo (JP)

(73) Assignee: Microbial Chemistry Research Foundation, Tokyo (JP)

( * ) Notice: Subject to any disclaimer, the term of this patent is extended or adjusted under 35 U.S.C. 154(b) by 448 days.

(21) Appl. No.: 13/403,018

(22) Filed: Feb. 23, 2012

(65) Prior Publication Data

US 2012/0184728 A1 Jul. 19, 2012

Related U.S. Application Data

(63) Continuation of application No. PCT/JP2010/064033, filed on Aug. 19, 2010.

(30) Foreign Application Priority Data

Aug. 25, 2009 (JP) ................................. 2009-194376

(51) Int. Cl.

| C07D 405/12 | (2006.01) |
|---|---|
| C12P 19/44 | (2006.01) |
| C07H 13/10 | (2006.01) |
| C07D 405/14 | (2006.01) |
| C12P 17/16 | (2006.01) |
| C12P 19/46 | (2006.01) |

(52) U.S. Cl.
CPC .............. *C07D 405/12* (2013.01); *C12P 19/44* (2013.01); *C07H 13/10* (2013.01); *C07D 405/14* (2013.01); *C12P 17/16* (2013.01); *C12P 19/46* (2013.01)
USPC ............. 536/17.3; 548/517; 548/537; 536/53

(58) Field of Classification Search
None
See application file for complete search history.

(56) References Cited

FOREIGN PATENT DOCUMENTS

| JP | 2009-203195 | 9/2009 |
|---|---|---|
| WO | 2005/100342 | 10/2005 |

OTHER PUBLICATIONS

Tohyama et al., "Biosynthesis of amycolamicin: the biosynthetic origin of a branched a-aminoethyl moiety in the unusual sugar amycolose" The Journal of Antibiotics (2010) vol. 63 pp. 147-149.*
*Amycolatopsis kentuckyensis* sp. nov., *Amycolatopsis lexingtonensis* sp. nov., and *Amycolatopsis pretoriensis* sp. nov., isolated from equine placentas, Labeda et al., International Journal of Systematic and Evolutionary Microbiology, vol. 53, pp. 1601-1605, 2003.
Two New Genera of Nocardioform Actinomycetes: *Amycolata* gen. nov. and *Amycolatopsis* gen. nov., Lechevalier et al., International Journal of Systematic Bacteriology, vol. 36, No. 1, pp. 29-37, 1986.

* cited by examiner

*Primary Examiner* — Eric Olson
(74) *Attorney, Agent, or Firm* — Carmody Torrance Sandak & Hennessey LLP

(57) ABSTRACT

A compound having a structure expressed by the following General Formula (1) or a salt thereof General Formula (1)

where "R" denotes a hydrogen atom or an alkyl group.

9 Claims, 5 Drawing Sheets

COMPOUND AMYCOLOSE DERIVATIVE, METHOD FOR PRODUCING THE SAME, AND USE OF THE SAME

CROSS-REFERENCE TO RELATED APPLICATION

This is a continuation application of PCT/JP2010/064033, filed on Aug. 19, 2010.

BACKGROUND OF THE INVENTION

1. Field of the Invention

The present invention relates to new compound amycolose derivatives, and a method for producing the same, and use of the same.

2. Description of the Related Art

From development to death, organisms involve repeated cell growth, cell differentiation and apoptosis to maintain their lives. Various diseases develop upon breakage of the mechanisms for regulating cells. Cancers are diseases where cells grow indefinitely due to abnormalities in regulation of cell growth. Cancers are difficult-to-treat diseases and rank high as death cause in the world.

Despite the recent advancement of cancer therapy, there has not yet been provided a therapeutic drug having a satisfactory cell growth suppressive activity capable of inhibiting the growth of cancer cells. Thus, at present, keen demand has arisen for a new compound having an excellent cell growth suppressive activity.

SUMMARY OF THE INVENTION

The present invention aims to solve the above existing problems and achieve the following objects. Specifically, an object of the present invention is to provide: a new compound easy to produce and having an excellent cell growth suppressive activity or a salt thereof; a method for producing the new compound or the salt thereof; and a pharmaceutical composition containing the new compound or the salt thereof.

In order to solve the above existing problems, the present inventors conducted extensive studies and have obtained the following findings: hydrolysis of a compound having a structure expressed by the following Structural Formula (4) with an acidic aqueous solution can produce a new compound having a structure expressed by the following Structural Formula (1); solvolysis of the compound having a structure expressed by the following Structural Formula (4) with an acidic alcohol solution can produce a new compound having a structure expressed by at least one of the following Structural Formulas (2) and (3); and these new compounds have an excellent cell growth suppressive activity. The present inventors have also confirmed that they each are a new compound through analysis of their chemical structure. The present invention has been accomplished on the basis of these findings. Notably, the present inventors named these new compounds "amycolose derivatives."

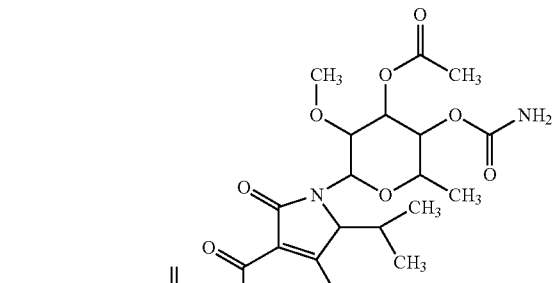

Structural Formula (4)

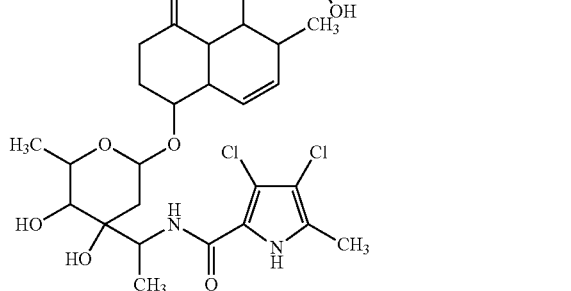

Structural Formula (1)

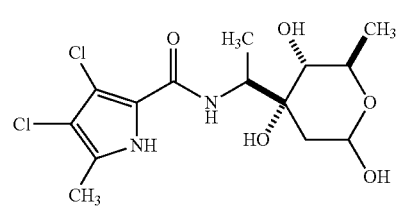

Structural Formula (2)

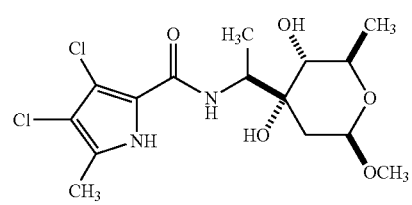

Structural Formula (3)

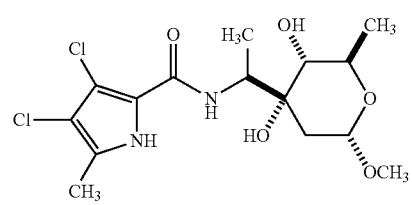

The compound having a structure expressed by the above Structural Formula (4) is a compound that was previously isolated by the present applicants and named "amycolamicin." The amycolamicin is produced from *Amycolatopsis* sp. MK575-fF5 strain (FERM P-21465) and has an excellent antibacterial activity.

The present invention is based on the above findings obtained by the present inventor. A compound or a salt thereof according to the present invention is represented by the following General Formula (1):

General Formula (1)

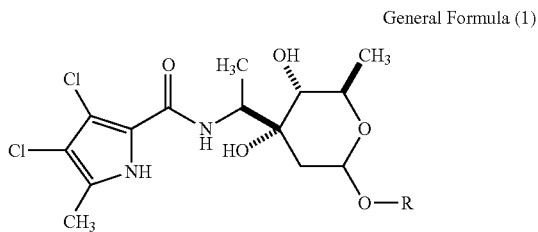

where "R" denotes a hydrogen atom or an alkyl group.

The present invention can provide: a new compound easy to produce and having an excellent cell growth suppressive activity or a salt thereof; a method for producing the new compound or the salt thereof and a pharmaceutical composition containing the new compound or the salt thereof. These can solve the above existing problems and achieve the above objects.

Figure 1:
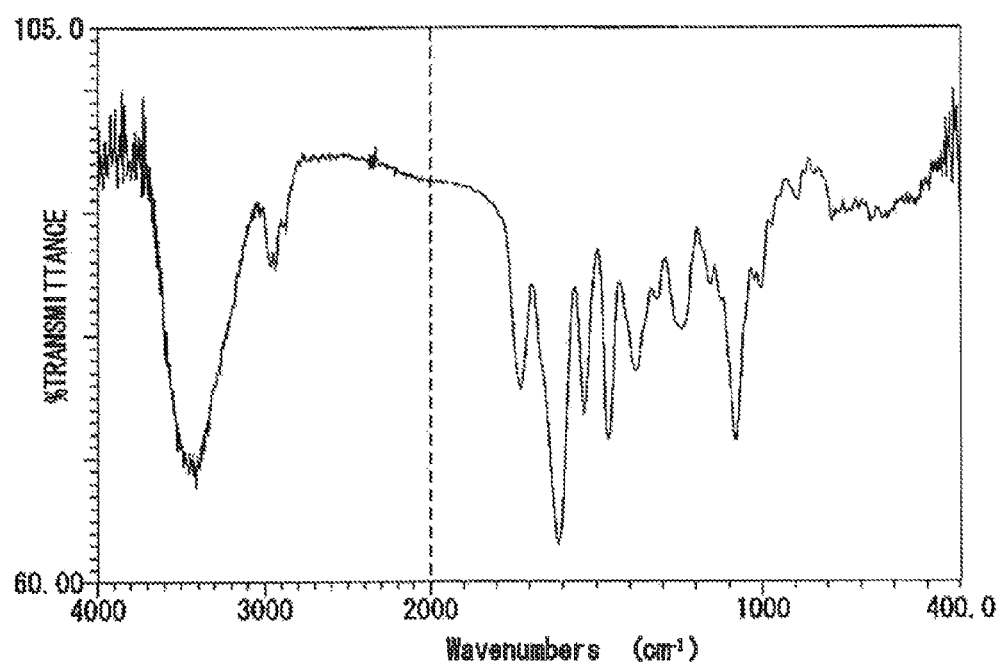
FIG. 1 is an infrared absorption spectrum chart of amycolamicin measured by the KBr tablet method, where vertical axis: transmittance (%) and horizontal axis: wavenumber ($cm^{-1}$).

DETAILED DESCRIPTION OF THE INVENTION (Compound or Salt thereof)

A compound of the present invention is represented by the following General Formula (1). The compound represented by the General Formula (1) is a new compound obtained by the present inventor and may be referred to as an "amycolose derivative":

General Formula (1)

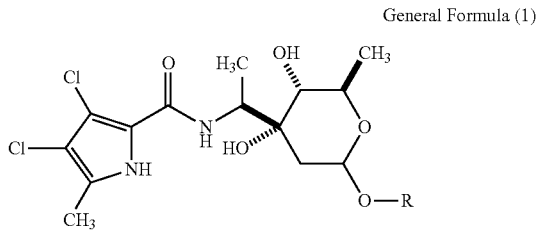

where "R" denotes a hydrogen atom or an alkyl group.
<Compound 1>

The amycolose derivative represented by the General Formula (1) where "R" is a hydrogen atom is a compound having a structure expressed by the following Structural Formula (1):

Structural Formula (1)

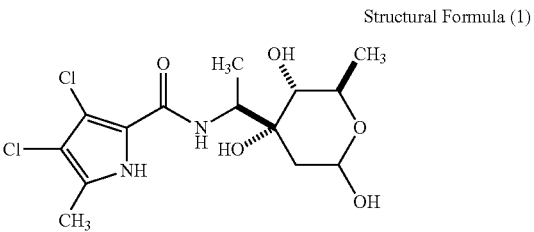 [SMILES: Cc1[nH]c(C(=O)N[C@@H](C)[C@]2(O)CC(O)O[C@H](C)[C@H]2O)c(Cl)c1Cl]

The following are physico-chemical properties of the compound having a structure expressed by the Structural Formula (1) (hereinafter may be referred to as "compound 1").

(1) Appearance: colorless syrup
(2) Molecular formula: $C_{14}H_{20}Cl_2N_2O_5$
(3) High resolution mass spectrometry (HRESIMS: positive ion mode)
 Found: m/z 389.0640 $(M+Na)^+$
 Calcd: m/z 389.0641 (as $C_{14}H_{20}Cl_2N_2O_5Na$)
(4) Specific rotation $[\alpha]_D^{23}=+15°$ (c0.51, chloroform)
(5) Peaks of $^1$H nuclear magnetic resonance spectra measured in deuterated chloroform at 30° C. and 600 MHz are as follows.
—α—Form of compound 1—
 δpm:1.20(3H,d,J=6.9 Hz),1.20(3H,d,J=6.2 Hz),1.72(1H, dd,J=3.8,14.1 Hz),1.84(1H,dd,J=1.4,14.1 Hz),2.23(3H,s), 3.07(1H,d,J=9.2 Hz),3.16(1H,t,J=9.2 Hz,),3.88(1H,dq, J=9.2,6.2 Hz),4.32(1H,pent.,J=7.2 Hz),4.97(1H,s),5.09(1H, dd,J=3.3,8.0 Hz),5.32(1H,d,J=9.0 Hz),6.74(1H,d,J=6.8 Hz), 10.20(1H,brs)
—β—Form of Compound 1—
 δpm:1.19(3H,d,J=6.2 Hz),1.20(3H,d,J=6.9 Hz),1.42(1H, dd,J=9.3,13.1 Hz), 1.80(1H,dd,J=2.1,13.1 Hz),2.23(3H,s), 3.02(1H,d,J=8.9 Hz),3.11(1H,t,8.9 Hz,),3.58(1H,dq,J=8.9, 6.2 Hz),3.92(1H,s),4.24(1H,d,J=6.2 Hz),4.31(1H,pent., J=7.4 Hz),4.94(1H,ddd,J=2.1,6.2,9.3 Hz),6.70(1H,d,J=6.6 Hz),10.20(1H,brs)
(6) Peaks of $^{13}$C nuclear magnetic resonance spectra measured in deuterated chloroform at 30° C. and 150 MHz are as follows.
—α—Form of Compound 1—
 δpm:11.1(q),16.2(q),18.5(q),38.8(t),52.3(d),71.1(d),74.3 (d),76.3(s),92.7(d),110.3(s),111.5(s),119.8(s),129.7(s), 161.0(s)
—β—Form of Compound 1—
 δpm:11.1(q),16.2(q),18.6(q),34.8(t),52.3(d),65.1(d),74.5 (d),77.2(s),93.3(d),110.2(s),111. 7(s),119.6(s),129.5(s), 161.2(s)

The analysis method usable for confirming that the compound 1 has a structure expressed by the Structural Formula (1) is not particularly limited and may be appropriately selected from various analysis methods depending on the intended purpose. Examples of the analysis method include a method of measuring, for example, mass spectrum, $^1$H nuclear magnetic resonance spectrum, $^{13}$C nuclear magnetic resonance spectrum or infrared absorption spectrum.

Also, the compound 1 may be in the form of a salt. The salt is not particularly limited and may be appropriately selected depending on the intended purpose. Examples thereof include: addition salts formed with inorganic acids such as hydrochloric acid and sulfuric acid; addition salts formed with organic acids such as formic acid, acetic acid, trifluoroacetic acid and tartaric acid; salts formed with alkali metals such as sodium and potassium; salts formed with alkaline earth metals such as calcium and magnesium; and salts formed with organic amines such as methylamine, ethylamine and diethanolamine.

Notably, the compound 1 has tautomerism and thus encompasses tautomers thereof.

The compound 1 or the salt thereof may be derived from the compound having a structure represented by the following Structural Formula (4) (hereinafter may be referred to as "amycolamicin") or may be obtained through chemical synthesis. Among them, the compound 1 or the salt thereof is preferably obtained by the below-described method of the present invention for producing the compound or the salt thereof.

Structural Formula (4)

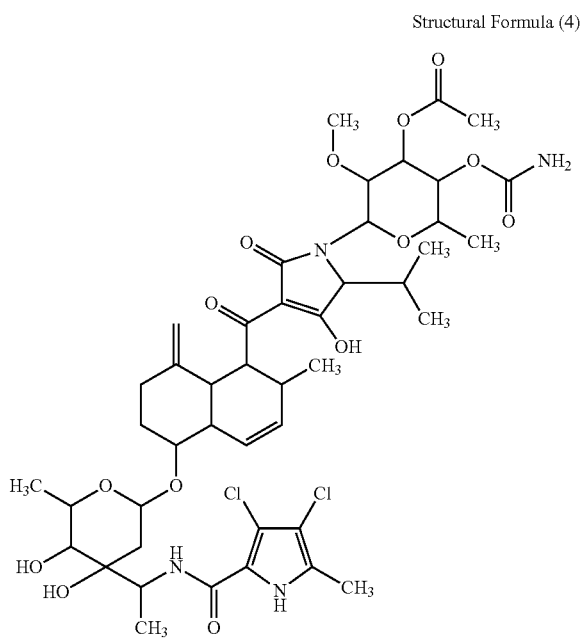 [SMILES: C=C1CCC(OC2CC(O)(C(C)NC(=O)c3[nH]c(C)c(Cl)c3Cl)C(O)C(C)O2)C2C=CC(C)C(C(=O)C3=C(O)C(C(C)C)N(C4OC(C)C(OC(N)=O)C(OC(C)=O)C4OC)C3=O)C12]

<Compounds 2 and 3>

The compound having a structure represented by the General Formula (1) where "R" is an alkyl group is not particularly limited, so long as "R" is an alkyl group, and may be appropriately selected depending on the intended purpose. It is preferably a compound where "R" is a methyl group, more preferably a compound having a structure expressed by at least one of the following Structural Formulas (2) and (3):

Structural Formula (2)

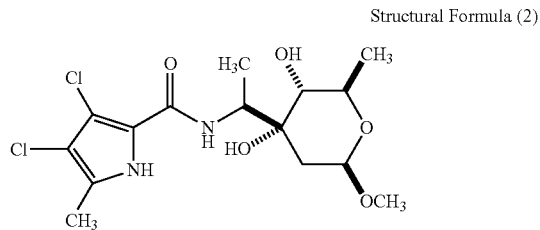

Structural Formula (3)

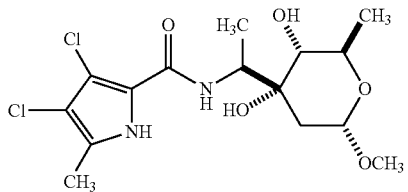

<<Compound 2>>

The following are physico-chemical properties of the compound having a structure expressed by the Structural Formula (2) (hereinafter may be referred to as "compound 2").

(1) Appearance: colorless syrup (2) Molecular formula: $C_{15}H_{22}Cl_2N_2O_5$ (3) High resolution mass spectrometry (HRESIMS: positive ion mode)

Found: m/z 403.0788 (M+Na)$^+$

Calcd: m/z 403.0798 (as $C_{15}H_{22}Cl_2N_2O_5Na$)

(4) Specific rotation $[\alpha]_D^{23}$=−113° (c0.24, chloroform)

(5) Peaks of $^1$H nuclear magnetic resonance spectra measured in deuterated chloroform at 30° C. and 600 MHz are as follows.

δpm:1.30(3H,d,J=7.3 Hz),1.34(3H,d,J=6.2 Hz),1.49(1H,dd, J=9.3,13.1 Hz),1.92(1H,dd,J=2.1,13.1 Hz),2.28(3H,s), 2.50(1H,brs),3.17(1H,brt,J=7.9 Hz),3.48(3H,s),3.64(1H, dq,J=9.3,6.2, Hz),4.42(1H,dq,J=7.3,6.2 Hz),4.69(1H,dd, J=2.1,9.3 Hz),5.22(1H,brs),6.63(1H,d,J=6.2 Hz),9.5-9.6 (1H,brs)

(6) Peaks of $^{13}$C nuclear magnetic resonance spectra measured in deuterated chloroform at 30° C. and 150 MHz are as follows.

δpm:11.4(q),16.1(q),18.0(q),36.3(t),52.6(d),55.6(q),70.4(d), 74.2(s),76.2(d),99.7(d),111.1(s),112.4(s),117.4(s), 128.7(s),161.3(s)

The analysis method usable for confirming that the compound 2 has a structure expressed by the Structural Formula (2) is not particularly limited and may be appropriately selected from various analysis methods depending on the intended purpose. Examples of the analysis method include a method of measuring, for example, mass spectrum, $^1$H nuclear magnetic resonance spectrum, $^{13}$C nuclear magnetic resonance spectrum or infrared absorption spectrum.

Also, the compound 2 may be in the form of a salt. The salt is not particularly limited and may be appropriately selected depending on the intended purpose. Examples thereof include: addition salts formed with inorganic acids such as hydrochloric acid and sulfuric acid; addition salts formed with organic acids such as formic acid, acetic acid, trifluoroacetic acid and tartaric acid; salts formed with alkali metals such as sodium and potassium; salts formed with alkaline earth metals such as calcium and magnesium; and salts formed with organic amines such as methylamine, ethylamine and diethanolamine.

The compound 2 or the salt thereof may be derived from amycolamicin or may be obtained through chemical synthesis. Among them, the compound 2 or the salt thereof is preferably obtained by the below-described method of the present invention for producing the compound or the salt thereof.

<<Compound 3>>

The following are physico-chemical properties of the compound having a structure expressed by the Structural Formula (3) (hereinafter may be referred to as "compound 3").
(1) Appearance: colorless syrup
(2) Molecular formula: $C_{15}H_{22}Cl_2N_2O_5$
(3) High resolution mass spectrometry (HRESIMS: positive ion mode)
 Found: m/z 403.0788 (M+Na)$^+$
 Calcd: m/z 403.0798 (as $C_{15}H_{22}Cl_2N_2O_5Na$)
(4) Specific rotation $[\alpha]_D^{23}$=+83° (c0.13, chloroform)
(5) Peaks of $^1$H nuclear magnetic resonance spectra measured in deuterated chloroform at 30° C. and 600 MHz are as follows.
 δpm:1.27(3H,d,J=6.8 Hz),1.33(3H,d,J=6.5 Hz),1.82(1H, dd,J=3.8,14.4 Hz),1.99(1H,dd,J=1.1,14.4 Hz),2.27(3H,s), 2.30(1H,brs),3.24(1H,brd,J=9.4 Hz),3.38(3H,s),3.68(1H,dq, J=9.4,6.5, Hz),4.14(1H,brs),4.42(1H,dq,J=8.6,6.8 Hz),4.84 (1H,brd,J=3.1 Hz),6.84(1H,d,J=8.6 Hz),9.74(1H,brs)
(6) Peaks of $^{13}$C nuclear magnetic resonance spectra measured in deuterated chloroform at 30° C. and 150 MHz are as follows.
 δpm:11.3(q),16.3(q),17.9(q),35.0(t),50.6(d),55.2(q),65.3 (d),73.4(s),74.2(d),98.2(d),110.3(s),110.9(s),118.7(s),127.6 (s),159.3(s)

The analysis method usable for confirming that the compound 3 has a structure expressed by the Structural Formula (3) is not particularly limited and may be appropriately selected from various analysis methods depending on the intended purpose. Examples of the analysis method include a method of measuring, for example, mass spectrum, $^1$H nuclear magnetic resonance spectrum, $^{13}$C nuclear magnetic resonance spectrum or infrared absorption spectrum.

Also, the compound 3 may be in the form of a salt. The salt is not particularly limited and may be appropriately selected depending on the intended purpose. Examples thereof include: addition salts formed with inorganic acids such as hydrochloric acid and sulfuric acid; addition salts formed with organic acids such as formic acid, acetic acid, trifluoroacetic acid and tartaric acid; salts formed with alkali metals such as sodium and potassium; salts formed with alkaline earth metals such as calcium and magnesium; and salts formed with organic amines such as methylamine, ethylamine and diethanolamine.

The compound 3 or the salt thereof may be derived from amycolamicin or may be obtained through chemical synthesis. Among them, the compound 3 or the salt thereof is preferably obtained by the below-described method of the present invention for producing the compound or the salt thereof.

<Application>

As shown in the below-described Test Example 1, the above amycolose derivatives or salts thereof have an excellent cell growth suppressive activity. Thus, the amycolose derivatives or the salts thereof can suitably be used as an active ingredient of the below-described pharmaceutical composition of the present invention.

(Method for Producing Compound or Salt thereof)

A method for producing the compound of the present invention; i.e., amycolose derivatives, or the salt thereof includes: culturing a microorganism belonging to the genus Amycolatopsis and capable of producing amycolamicin or a salt thereof, isolating the amycolamicin or the salt thereof from a culture obtained from the culturing; and decomposing the amycolamicin or the salt thereof.

In general, physiologically active compounds produced by microorganisms have complex structures and thus are difficult to produce through synthetic organic chemistry. However, derivatives having their partial structures essential for development of physiological activities can easily be obtained, and used for the synthesis of compounds having a higher cell growth suppressive activity, which is advantageous.

<Method for Producing Amycolamicin>

The amycolamicin is produced as follows. Specifically, microorganisms that produce the amycolamicin (hereinafter may be referred to as "amycolamicin-producing microorganisms") are inoculated into a nutrient medium and cultured at a temperature suitable for the production of the amycolamicin, whereby a culture containing the amycolamicin is obtained.

The nutrient medium used for the above culturing is nutrient media that can be used for culturing actinomycetes. Examples of the nutrient sources which can be added to the nutrient medium include nitrogen sources such as commercially available soy flour, peptone, yeast extract, meat extract, corn steep liquor and ammonium sulfate; carbon sources such as fats and carbohydrates; e.g., tomato paste, glycerin, starch, glucose, galactose and dextrin. In addition, inorganic salts such as sodium chloride and calcium carbonate may be added to the medium before use. If necessary, a trace amount of a metal salt may be added to the medium before use. Any known material for culturing actinomycetes may be used so long as the material can be utilized by the amycolamicin-producing microorganisms to promote the production of the amycolamicin.

The production of the amycolamicin uses the microorganism belonging to the genus Amycolatopsis and capable of producing the amycolamicin. Specifically, a microorganism of Amycolatopsis sp. MK575-fF5 strain (FERM P-21465) can produce the amycolamicin. Also, other strains that are capable of producing the amycolamicin can be isolated from the natural world by a routine method for insolating amycolamicin-producing microorganisms. Notably, through mutation treatments such as exposure to radiation, the microorganism of Amycolatopsis sp. MK575-fF5 strain and other microorganisms capable of producing the amycolamicin can be mutated so that they have increased production capability of the amycolamicin. Moreover, the amycolamicin can be produced through genetically engineering techniques.

The seed culture used for the production of the amycolamicin may be, for example, the growth culture obtained through slant culturing of the amycolamicin-producing bacteria on an agar medium For the production of the amycolamicin, it is preferred that the amycolamicin-producing bacteria be aerobically cultured in an appropriate medium. Also, for isolating the target compound from the resultant culture, a routine method can be used. The culturing temperature is not particularly limited and may be determined depending on the type of the amycolamicin-producing microorganisms, so long as the growth of the amycolamicin-producing microorganisms is not substantially inhibited and the amycolamicin-producing microorganisms can produce the amycolamicin. The culturing temperature is preferably 25° C. to 35° C.

For example, the production of the amycolamicin by the Amycolatopsis sp. MK575-fF5 strain generally becomes maximum for 3 days to 9 days. A change over time in the titer of the amycolamicin in the culture can be measured through, for example, HPLC or a cylinder plate method using Staphylococcus aureus or other bacteria as tested bacteria.

In the above production method, the amycolamicin is isolated from the obtained culture. The isolation method may appropriately utilize a method used for isolating metabolites produced by microorganisms. Examples of the isolation method for the amycolamicin include a method by extracting with a water-immiscible solvent, a method utilizing differences in adsorption affinity to various adsorbents, gel filtration, chromatography utilizing countercurrent distribution, and combinations thereof. The separated microorganisms are treated with an extracting method using an appropriate organic solvent or an eluting method through disruption of microorganisms, whereby the amycolamicin can be isolated through extraction of the microorganisms and isolation/purification as described above.

The production method can be performed as described above to produce the amycolamicin. Notably, the amycolamicin has tautomerism and thus encompasses tautomers thereof.

Since the amycolamicin is an acidic compound, the amycolamicin or the salts thereof can generally be produced by a known method using, for example, pharmaceutically acceptable various metals (e.g., alkali metals) or organic bases (e.g., quaternary ammonium salts).

—Microorganism—

The above microorganism belongs to the genus *Amycolatopsis* and is capable of producing the amycolamicin or the salt thereof. The microorganism is not particularly limited and may be appropriately selected depending on the intended purpose, so long as it belongs to the genus *Amycolatopsis* and is capable of producing the amycolamicin or the salt thereof, and thus can be used as the amycolamicin-producing microorganisms in the above-described production method for the amycolamicin or the salt thereof.

In particular, preferably used are actinomycetes isolated from the soil of Sendai-shi, Miyagi and given accession number MK575-fF5 strain in May, 1996 by the microbial chemistry research center of Microbial Chemistry Research Foundation. The mycological characteristics of the MK575-fF5 strain are as follows.

1. Morphology

Substrate hyphae are well branched in a zigzag form and are divided. Aerial hyphae are grown in some cases or not grown in other cases. When aerial hyphae are grown, the aerial hyphae are relatively long and linear or irregularly curved as well as divided into cylindrical spores. The surface is smooth and the size is about 0.4 µm to about 0.6 µm×about 0.8 µM to about 2.2 µm. Also, the aerial hyphae may be tangled together to have a spherical shape. Whorls, mycelial strands, sporangia and motile spores are not observed.

2. Growth Conditions in Various Media

The standards in blankets relating to colors are based on the color harmony manual of Container Corporation of America.

(1) Yeast-malt agar medium (ISP-medium 2, culturing at 27° C.)

This strain is grown in pale yellow [2 gc, Bamboo] and slightly forms white aerial hyphae in some cases or does not form them in other cases. Soluble dyes are not produced.

(2) Oatmeal agar medium (ISP-medium 3, culturing at 27° C.)

This strain is grown in pale yellow [2 gc, Bamboo] and slightly forms white aerial hyphae in some cases or does not form them in other cases. Soluble dyes are not produced.

(3) Starch-inorganic salt agar medium (ISP-medium 4, culturing at 27° C.)

This strain is grown in pale yellow [2 ea, Lt Wheat] to dull yellow [3 nc, Amber] and slightly forms white aerial hyphae in some cases. Soluble dyes are not produced.

(4) Glycerin-asparagine agar medium (ISP-medium 5, culturing at 27° C.)

This strain is grown in dull yellowish orange [31c, Amber] and forms aerial hyphae of pale orange [4 ea, Light Apricot] in some cases or does not form them in other cases. Soluble dyes are not produced.

(5) Tyrosine agar medium (ISP-medium 7, culturing at 27° C.)

This strain is grown in pale yellow [3 ca, Pearl Pink] to dull yellowish orange [3 lc, Amber] and forms aerial hyphae of pale orange [4 ca, Fresh Pink] in some cases or does not form them in other cases. Soluble dyes are not produced.

(6) Sucrose-nitrate agar medium (culturing at 27° C.)

This strain is grown in colorless to pale yellowish orange [3 ea, Lt Melon Yellow] and slightly forms white aerial hyphae in some cases or does not form them in other cases. Soluble dyes are not produced.

3. Physiological Properties (1) Temperature range of growth

This strain was cultured on a glucose-aspartic acid agar medium (glucose: 1.0% by mass, L-aspartic acid: 0.05% by mass, dipotassium hydrogenphosphate: 0.05% by mass, string agar; 3.0% by mass, pH 7.0) at a temperature of 10° C., 20° C., 24° C., 27° C., 30° C., 37° C., 45° C. or 50° C. As a result, the strain was not grown at 10° C., 45° C. or 50° C. but was grown at 20° C. to 37° C. The optimal growth temperature is about 30° C.

(2) Hydrolysis of starch (starch-inorganic salt agar medium, ISP-medium 4, culturing at 27° C.)

Negative on day 21 from the beginning of the culturing (3) Production of melanine-like dye (tripton-yeast-broth, ISP-medium 1; peptone-yeast-iron agar medium, ISP-medium 6; tyrosine agar medium, ISP-medium 7; culturing at 27° C. for each medium)

Negative for each medium (4) Availability of carbon source (Pridham-Godleave agar medium, ISP-medium 9; culturing at 27° C.)

This strain is grown by utilizing D-glucose, L-arabinose, D-xylose, D-fructose, sucrose, inositol, rhamnose, raffinose and D-mannitol.

(5) Reduction reaction of nitrate (0.1% by mass potassium nitrate-containing peptone water, ISP-medium 8, culturing at 27° C.)

Positive

4. Microbial Components (1) Composition of cell wall

The cell wall contains meso-2,6-diaminopimelic acid.

(2) Reducing sugar in each microorganism

Each microorganism contains arabinose and galactose (Type A).

(3) Isoprenoid quinone

MK-9 ($H_4$) and a small amount of MK-10 ($H_4$) are contained as main menaquinone.

(4) Phospholipid

Type PII (phosphatidylethanolamine is contained but phosphatidyl choline and unknown glucosamine-containing phospholipids are not contained)

(5) Mycolic acid

Not contained.

5. Analysis of 16S rRNA Gene

A partial nucleotide sequence (1,455 nt) of the 16S rRNA gene was determined and searched for homology based on international nucleotide sequence database (GenBank/DDBJ/EMBL). As a result, the nucleotide sequence of the MK575-fF5 strain was found to have high homology with those of the 16S rRNA genes of actinomycetes belonging to the genus *Amycolatopsis*; i.e., *Amycolatopsis kentuckyensis* (99.1%), *Amycolatopsis rifamycinica* (99.03%), *Amycolatopsis mediterranei* (98.9%), and *Amycolatopsis balhi-*

*mycetica* (98.82%). Note that the values in parentheses are homology between the nucleotide sequences.

In summary, substrate hyphae of the MK575-fF5 strain are in a zigzag form and divided. Aerial hyphae are linear or irregularly curved and divided into cylindrical spores. Whorls, mycelial strands, sporangia and motile spores are not observed. The MK575-fF5 strain is grown in colorless to yellowish orange in various media. Aerial hyphae of white to pale orange are formed in some cases or not formed in other cases. Soluble dyes are not produced. The optimal growth temperature is about 30° C. This strain is negative in terms of the production of melanine-like dye and the hydrolysis of starch, but is positive in terms of reduction reaction of nitrate.

Regarding the microbial components of the MK575-fF5 strain, the hydrolyzates of each microorganism contain meso-2,6-diaminopimelic acid, arabinose and galactose, the cell wall is of Type IV, and the reducing sugars of each microorganism are of Type A. Also, mycolic acid is not contained and phospholipid is of Type PII (phosphatidylethanolamine is contained but phosphatidyl choline and unknown glucosamine-containing phospholipids are not contained) as well as a main menaquinone is MK-9($H_4$).

Through comparison of the partial nucleotide sequence of the 16S rRNA gene with corresponding data of known bacterial strains, the nucleotide sequence was found to have high homology with those of actinomycetes belonging to the genus *Amycolatopsis*.

In conclusion, the MK575-fF5 strain was thought to belong to the genus *Amycolatopsis* (International Journal of Systematic Bacteriology, Vol. 36, pp. 29-37, 1986). Then, the MK575-fF5 strain was designated *Amycolatopsis* sp. MK575-fF5 strain. Notably, the MK575-fF5 strain was requested for deposition to the National Institute of Advanced Industrial Science and Technology, International Patent Organism Depositary and was accepted as FERM P-21465 on Dec. 12, 2007.

<Method for Producing Amycolose Derivative>

A method for producing the amycolose derivatives or the salts thereof is not particularly limited and may be appropriately selected depending on the intended purpose. It is preferably a method including decomposing the amycolamicin or the salt thereof.

The method for the decomposing is not particularly limited and may be appropriately selected depending on the intended purpose. Examples thereof include a hydrolysis method and a solvolysis method. For the production of the compound 1 or the salt thereof, the hydrolysis method is preferably used. For the production of at least one of the compounds 2 and 3 or the salts thereof, the solvolysis method is preferably used.

—Hydrolysis Method—

The hydrolysis method is not particularly limited and may be appropriately selected depending on the intended purpose. It is preferably a hydrolysis method in which hydrolysis is performed with an acidic aqueous solution.

The acidic aqueous solution is not particularly limited and may be appropriately selected depending on the intended purpose. Examples thereof include an acetic acid aqueous solution, a sulfuric acid aqueous solution, a nitric acid aqueous solution and a hydrogen chloride aqueous solution. The above acidic aqueous solutions may be used alone or in combination.

The temperature at which the hydrolysis is performed is not particularly limited and may be appropriately selected depending on the intended purpose, but is preferably 0° C. to 100° C., more preferably 20° C. to 40° C.

The time for which the hydrolysis is performed is not particularly limited and may be appropriately selected depending on the intended purpose, but is preferably 0.5 hours to 24 hours, more preferably 1 hour to 3 hours.

The method for terminating the hydrolysis reaction is not particularly limited and may be appropriately selected depending on the intended purpose. The hydrolysis reaction is terminated with, for example, any of a saturated sodium bicarbonate aqueous solution and various buffers.

The reaction mixture obtained after the hydrolysis is preferably extracted with a solvent since the compound 1 or the salt thereof can be obtained at higher concentrations.

The solvent is not particularly limited and may be appropriately selected depending on the intended purpose. Examples thereof include ethyl acetate, diethyl ether, chloroform and dichloromethane.

The method for purifying the compound 1 after the extraction is not particularly limited and may be appropriately selected depending on the intended purpose. Examples thereof include a method utilizing differences in adsorption affinity to various adsorbents, gel filtration, chromatography utilizing countercurrent distribution, and combinations thereof.

—Solvolysis Method—

The solvolysis method is not particularly limited and may be appropriately selected depending on the intended purpose. It is preferably a solvolysis method in which solvolysis is performed with an alcohol solution, more preferably a solvolysis method in which solvolysis is performed with an acidic alcohol solution.

The alcohol solution is not particularly limited and may be appropriately selected depending on the intended purpose. Examples thereof include methanol, ethanol, n-propyl alcohol, i-propyl alcohol and n-butanol. The above alcohol solutions may be used alone or in combination.

The acid contained in the acidic alcohol solution is not particularly limited and may be appropriately selected depending on the intended purpose. Examples thereof include acetic acid, sulfuric acid, nitric acid and hydrogen chloride. These acids may be used alone or in combination.

The temperature at which the solvolysis is performed is not particularly limited and may be appropriately selected depending on the intended purpose, but is preferably 0° C. to 100° C., more preferably 20° C. to 40° C.

The time for which the solvolysis is performed is not particularly limited and may be appropriately selected depending on the intended purpose, but is preferably 0.5 hours to 24 hours, more preferably 1 hour to 3 hours.

The method for terminating the solvolysis reaction is not particularly limited and may be appropriately selected depending on the intended purpose. The hydrolysis reaction is terminated with, for example, any of a saturated sodium bicarbonate aqueous solution and various buffers.

The reaction mixture obtained after the solvolysis is preferably extracted with a solvent since at least one of the compounds 2 and 3 or the salts thereof can be obtained at higher concentrations.

The solvent is not particularly limited and may be appropriately selected depending on the intended purpose. Examples thereof include ethyl acetate, diethyl ether, chloroform and dichloromethane.

The method for purifying at least one of the compounds 2 and 3 or the salt thereof after the extraction is not particularly limited and may be appropriately selected depending on the intended purpose. Examples thereof include a method utilizing differences in adsorption affinity to various adsorbents, gel filtration, chromatography utilizing countercurrent distribution, and combinations thereof.

(Pharmaceutical Composition)

A pharmaceutical composition of the present invention contains the above-described amycolose derivative(s) (at least one of the compounds 1, 2 and 3) or the salts thereof; and, if necessary, further contains other ingredients.

<Amycolose Derivative>

The amount of the amycolose derivative(s) (at least one of the compounds 1, 2 and 3) or the salts thereof contained in the pharmaceutical composition is not particularly limited and may be appropriately selected depending on the intended purpose. Also, the pharmaceutical composition may be the amycolose derivative(s) or the salt thereof themselves.

<Other Ingredients>

The other ingredients are not particularly limited and may be appropriately selected from pharmacologically acceptable carriers depending on the intended purpose. Specific examples thereof include ethanol, water and starch. The amount of the other ingredients contained in the pharmaceutical composition is not particularly limited and may be appropriately selected depending on the intended purpose, so long as the effects of the amycolose derivative(s) (at least one of the compounds 1, 2 and 3) or the salt thereof are not impeded.

<Dosage Form>

The dosage form of the pharmaceutical composition is not particularly limited and may be appropriately selected depending on the intended purpose. Examples of the dosage form include an oral solid preparation, an oral liquid preparation, an injection and an inhalation powder.

—Oral Solid Preparation—

The oral solid preparation is not particularly limited and may be appropriately selected depending on the intended purpose. Examples of the oral solid preparation include a tablet, a coated tablet, granules, powder and a capsule.

The method for producing the oral solid preparation is not particularly limited and may be a routine method. For example, the oral solid preparation can be produced by adding an excipient and, if necessary, the above other ingredients and various additives to the amycolose derivative(s) (at least one of the compounds 1, 2 and 3) or the salt thereof. Here, the excipient is not particularly limited and may be appropriately selected depending on the intended purpose. Examples of the excipient include lactose, sucrose, sodium chloride, glucose, starch, calcium carbonate, kaolin, microcrystalline cellulose and silicic acid. The additives are not particularly limited and may be appropriately selected depending on the intended purpose. Examples of the additives include a binding agent, a disintegrating agent, a lubricating agent, a coloring agent and a sweetening/flavoring agent.

The binding agent is not particularly limited and may be appropriately selected depending on the intended purpose. Examples of the binding agent include water, ethanol, propanol, simple syrup, glucose liquid, starch liquid, gelatine liquid, carboxymethylcellulose, hydroxypropylcellulose, hydroxypropylstarch, methylcellulose, ethylcellulose, shellac, calcium phosphate and polyvinylpyrrolidone.

The disintegrating agent is not particularly limited and may be appropriately selected depending on the intended purpose. Examples of the disintegrating agent include dry starch, sodium alginate, powdered agar, sodium hydrogencarbonate, calcium carbonate, sodium lauryl sulfate, monoglyceride stearate and lactose.

The lubricating agent is not particularly limited and may be appropriately selected depending on the intended purpose. Examples of the lubricating agent include purified talc, stearic acid salts, borax and polyethylene glycol.

The coloring agent is not particularly limited and may be appropriately selected depending on the intended purpose. Examples of the coloring agent include titanium oxide and iron oxide.

The sweetening/flavoring agent is not particularly limited and may be appropriately selected depending on the intended purpose. Examples of the sweetening/flavoring agent include sucrose, orange peel, citric acid and tartaric acid.

—Oral Liquid Preparation—

The oral liquid preparation is not particularly limited and may be appropriately selected depending on the intended purpose. Examples of the oral liquid preparation include an internal liquid, syrup and elixir.

The method for producing the oral liquid preparation is not particularly limited and may be a routine method. For, example, the oral liquid preparation can be produced by adding an excipient and, if necessary, the above other ingredients and various additives to the amycolose derivative(s) (at least one of the compounds 1, 2 and 3) or the salt thereof. Here, the additives are not particularly limited and may be appropriately selected depending on the intended purpose. Examples of the additives include a sweetening/flavoring agent, a buffer and a stabilizing agent.

The sweetening/flavoring agent is not particularly limited and may be appropriately selected depending on the intended purpose. Examples of the sweetening/flavoring agent include sucrose, orange peel, citric acid and tartaric acid.

The buffer is not particularly limited and may be appropriately selected depending on the intended purpose. Examples of the buffer include sodium citrate.

The stabilizing agent is not particularly limited and may be appropriately selected depending on the intended purpose. Examples of the stabilizing agent include tragacanth, gum arabic and gelatin.

—Injection—

The injection is not particularly limited and may be appropriately selected depending on the intended purpose. Examples of the injection include a solution, a suspension and a solid preparation reconstituted upon use.

The method for producing the injection is not particularly limited and may be a routine method. For example, the injection can be produced by optionally adding the above other ingredients, a pH adjuster, a buffer, a stabilizing agent, a tonicity agent and a local anesthetic to the amycolose derivative(s) (at least one of the compounds 1, 2 and 3) or the salt thereof. Here, the pH adjuster or buffer is not particularly limited and may be appropriately selected depending on the intended purpose. Examples of the pH adjuster or buffer include sodium citrate, sodium acetate and sodium phosphate. The stabilizing agent is not particularly limited and may be appropriately selected depending on the intended purpose. Examples of the stabilizing agent include sodium pyrosulfite, EDTA, thioglycolic acid and thiolactic acid. The tonicity agent is not particularly limited and may be appropriately selected depending on the intended purpose. Examples of the tonicity agent include sodium chloride and glucose. The local anesthetic is not particularly limited and may be appropriately selected depending on the intended purpose. Examples of the local anesthetic include procaine hydrochloride and lidocaine hydrochloride.

<Administration>

Regarding the pharmaceutical composition, the administration method, the administration dose, the timing of administration and the subject to be administered are not particularly limited and may be appropriately selected depending on the intended purpose.

The administration method is not particularly limited and may be appropriately selected depending on the intended purpose. Examples of the administration method include oral administration, injection and inhalation.

The administration dose is not particularly limited and may be appropriately selected considering various factors of a subject to be administered, such as the age, body weight, constitution, symptom and the presence or absence of administration of a drug containing other active ingredients.

The animal species serving as the subject to be administered is not particularly limited and may be appropriately selected depending on the intended purpose. Examples of the animal species include human, monkey, pig, bovine, sheep, goat, dog, cat, mouse, rat and bird. Among them, the pharmaceutical composition is suitably administered to human.
<Use>

The pharmaceutical composition may be used alone or in combination with a drug containing other active ingredients. Also, the pharmaceutical composition may be formulated into a drug containing other active ingredients before use.
<Application>

The pharmaceutical composition contains as an active ingredient(s) the amycolose derivative(s) (at least one of the compounds 1, 2 and 3) or the salt thereof, and thus has an excellent cell growth suppressive activity as shown in the below-described Test Example 1. Therefore, the pharmaceutical composition can suitably be used as a cell growth suppressive agent and is useful for the prevention or treatment of cancer.

EXAMPLES

The present invention will next be described in more detail by way of Examples, which should not be construed as limiting the present invention thereto.

Example 1

Production of Compound 1

Cells of *Amycolatopsis* sp. MK575-fF5 strain (deposited as FERM P-21465) were cultured in an agar slant medium. Separately, a liquid medium containing galactose 2% by mass, dextrin 2% by mass, glycerin 1% by mass, Bacto Soytone (product of Difco Co., Ltd.) 1% by mass, corn steep liquor 0.5% by mass, ammonium sulfate 0.2% by mass and calcium carbonate 0.2% by mass (the pH of the liquid medium being adjusted to 7.4) was dispensed in 500 mL-conical flasks so that each conical flask contained 110 mL of the liquid medium, followed by routinely sterilizing at 120° C. for 20 min. The above-cultured cells were inoculated in the liquid medium. Thereafter, the cells were shake-cultured through rotation at 30° C. for 4 days, to thereby obtain seed culture liquids.

A medium (100 L) having the following composition: glycerin 0.5% by mass, dextrin 0.5% by mass, Bacto Soytone (product of Difco Co., Ltd.) 0.25% by mass, yeast extract (product of NIHON PHARMACEUTICAL CO., LTD.) 0.075% by mass, . ammonium sulfate 0.05% by mass and calcium carbonate 0.05% by mass (the pH of the medium being adjusted to 7.4) was prepared in a 200 L-culturing tank, followed by sterilizing, to thereby obtain a production medium. Two percent by volume of each seed culture was inoculated in the production medium, followed by culturing in the tank for four days under the following conditions: 27° C., 200 rpm, air flow rate: 100 L/min.

The thus-obtained culture was centrifuged so as to be separated into 80 L of the culture filtrate and 2.5 kg of the microorganisms. Subsequently, 12 L of methanol was added to the microorganisms, and the resultant mixture was thoroughly stirred. Then, the compound having a structure expressed by the following Structural Formula (4) (hereinafter may be referred to as "amycolamicin") was extracted from the microorganisms with methanol, followed by removal of methanol under reduce pressure, to thereby obtain 2 L of a microorganism extract containing amycolamicin. Then, 6 L of ethyl acetate was added to the microorganism extract (2 L), and the resultant mixture was thoroughly stirred so that amycolamicin was extracted with ethyl acetate. The resultant mixture treated with 6 L of ethyl acetate was dried with anhydrous sodium sulfate and then concentrated and dried under reduced pressure, to thereby obtain 18 g of a crude product containing amycolamicin. Hexane (200 mL) was added to 18 g of the crude product containing amycolamicin and the hexane-soluble ingredients were removed, to thereby obtain 3.3 g of a hexane-insoluble fraction containing amycolamicin. The hexane-insoluble fraction (3.3 g) containing amycolamicin was dissolved in methanol, and the resultant solution was chromatographically separated with a Sephadex LH-20 (inner diameter: 28 mm×length: 450 mm, product of Pharmacia Biotech Inc.) column. The solution was fractionated every 8 g (one fraction) and, as a result, the active fractions were eluted as fractions 12 to 15. The fractions were collected and concentrated and dried under reduced pressure, to thereby obtain 1,584 mg of a crude product containing amycolamicin. The thus-obtained crude product. (1,584 mg) was dissolved in a small amount of methanol, and 50 mL of kieselguhr (product of Merck Co.) was added to the resultant solution. Then, the solvent was concentrated and dried under reduced pressure. The kieselguhr was applied to a silica gel column (inner diameter: 32 mm×length: 175 mm, product of Merck Co.) to perform chromatography. The developing solvents sequentially used were chloroform : methanol : water=100:0:0 (200 mL), 95:5:0 (450 mL), 1:95:5:0.25 (450 mL) and 1:90:10:0.5 (450 mL). The chromatography was fractionated every 18 g (one fraction) and, as a result, amycolamicin was eluted as fractions 76 to 103. The fractions were collected and concentrated and dried under reduced pressure, to thereby obtain 827 mg of pure amycolamicin.

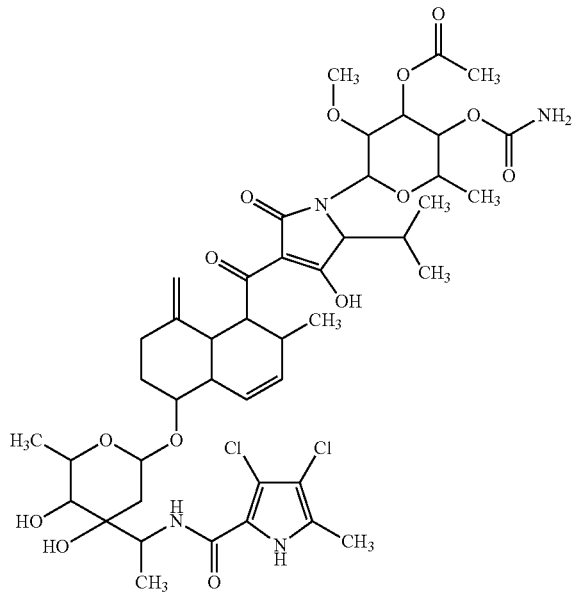

Structural Formula (4)

Through analysis of the obtained amycolamicin for physico-chemical properties, it was found to have the physico-chemical properties as shown below. From the physico-chemical properties, it was confirmed that the amycolamicin was the compound having a structure expressed by the following Structural Formula (4). Also, this amycolamicin was found to have tautomerism.

Figure 2:
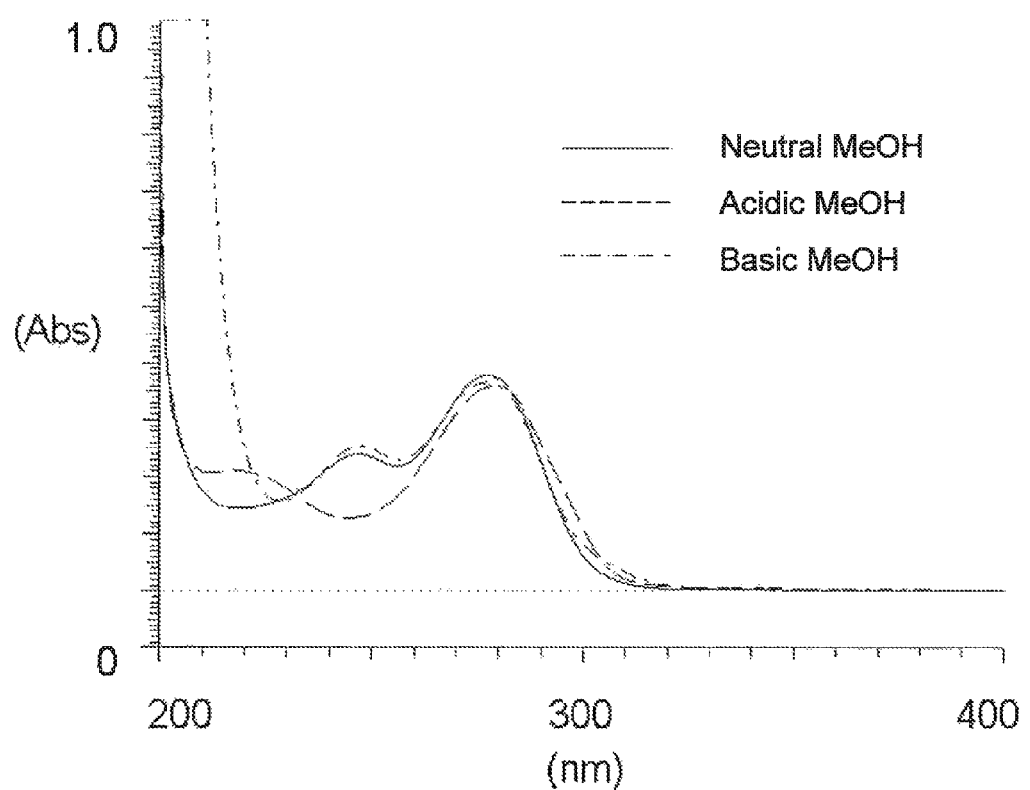
FIG. 2 is a UV absorption spectrum chart of amycolamicin measured in methanol, where vertical axis: absorbance (Abs) and horizontal axis: wavelength (nm).
Figure 3:
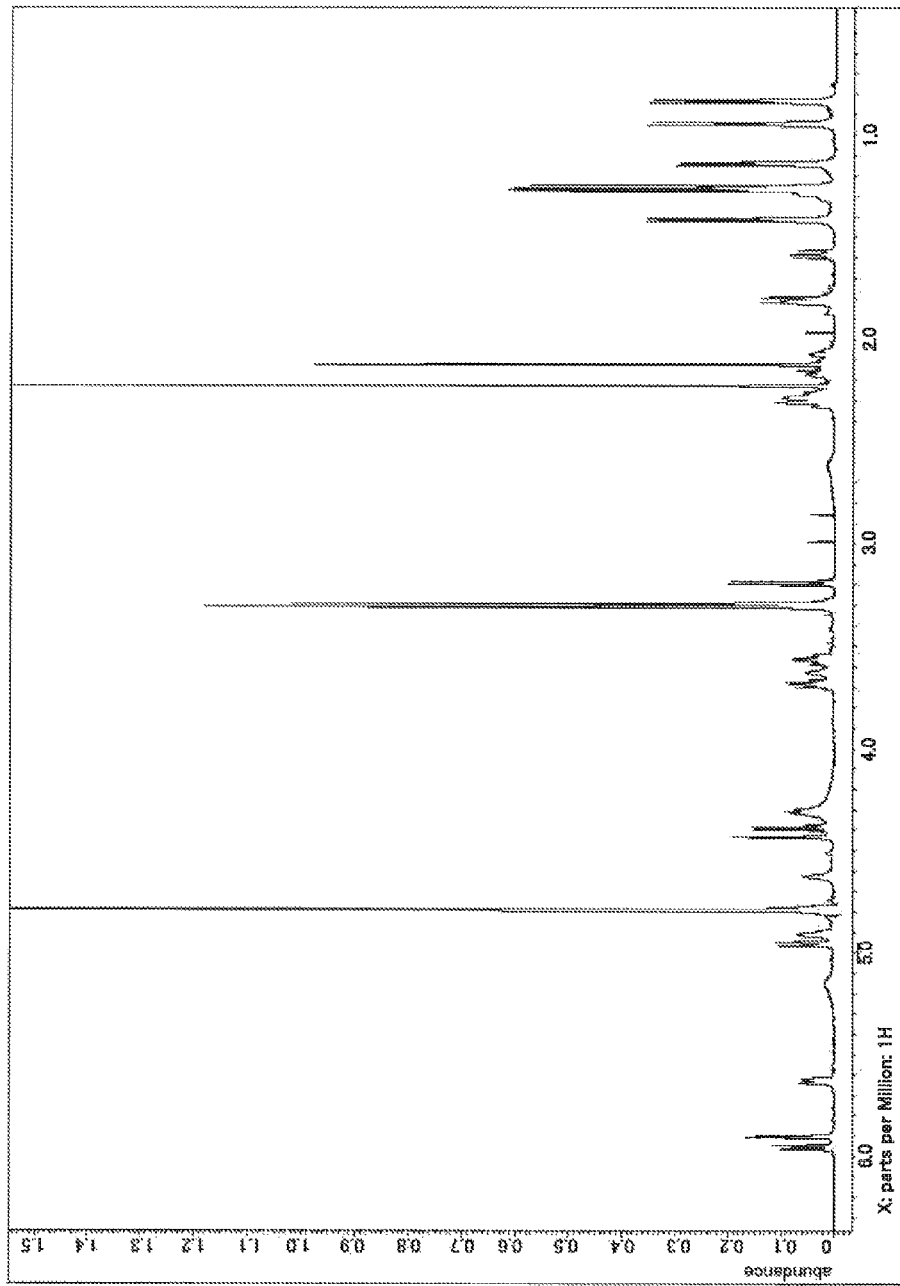
FIG. 3 is a $^1$H nuclear magnetic resonance spectrum chart of amycolamicin measured in deuterated methanol at 30° C. and 600 MHz, where the unit of the horizontal axis: ppm.
Figure 4:
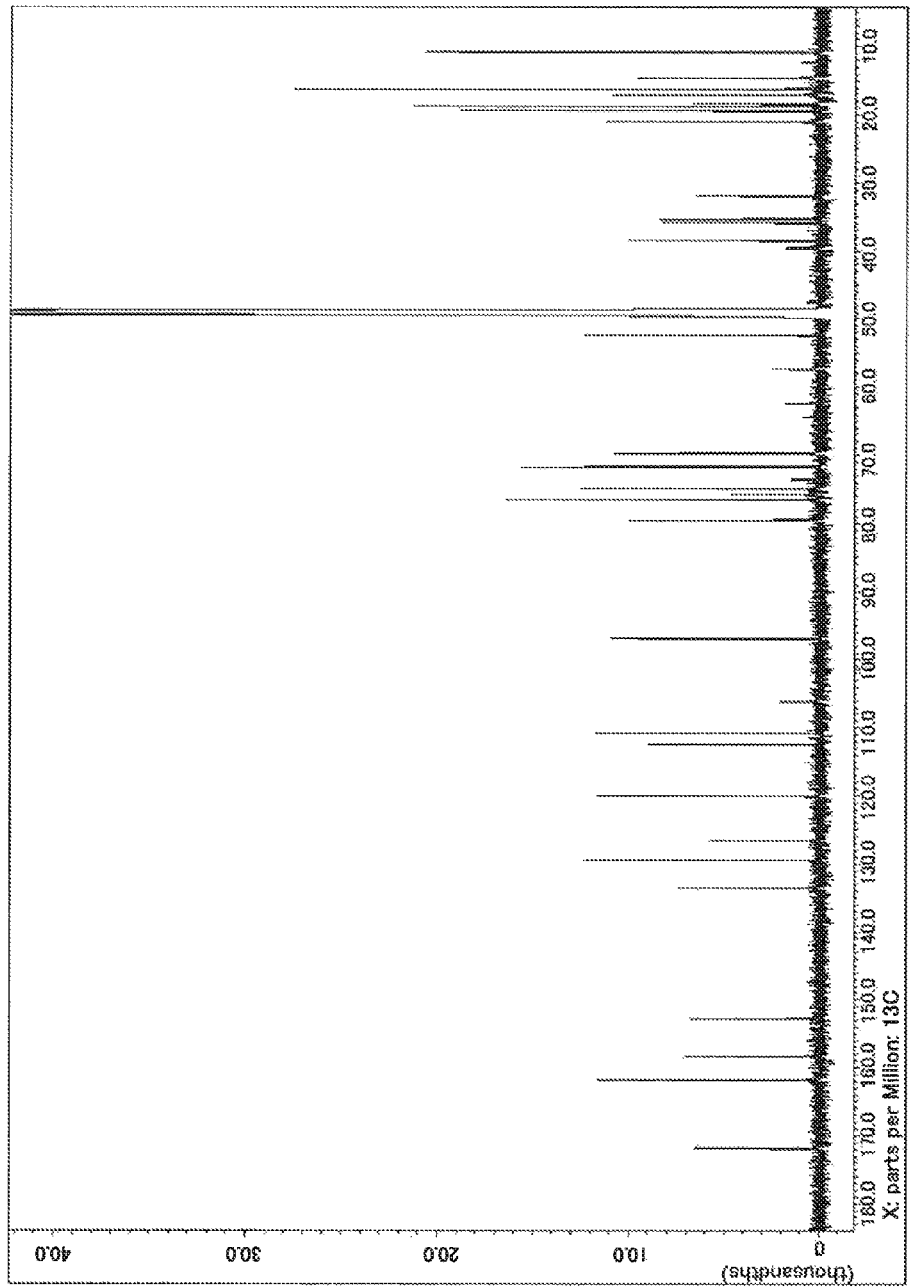
FIG. 4 is a $^{13}$C NMR spectrum chart of amycolamicin measured in deuterated methanol at 30° C. and 150 MHz, where the unit of the horizontal axis: ppm.

(1) Appearance: white powder
(2) Molecular formula: $C_{44}H_{60}Cl_2N_4O_{14}$
(3) High resolution mass spectrometry (HRESIMS: negative ion mode)
  Found: m/z 937.3386 (M−H)⁻
  Calcd: m/z 937.3405 (as $C_{44}H_{59}Cl_2N_4O_{14}$)
(4) Specific rotation $[\alpha]_D^{23}$=−21.6° (c0.5, methanol)
(5) Infrared absorption spectrum is as shown in FIG. 1.
(6) UV absorption spectrum is as shown in FIG. 2.
(7) ¹H nuclear magnetic resonance spectrum measured in deuterated methanol at 30° C. and 600 MHz is as shown in FIG. 3.
(8) ¹³C nuclear magnetic resonance measured in deuterated methanol at 30° C. and 150 MHz is as shown in FIG. 4.
(9) Thin-layer chromatography using silica gel 60F₂₅₄ (product of Merck Co.) and a developing solvent of chloroform methanol (90 10 by volume), the Rf value is 0.31.

Structural Formula (4)

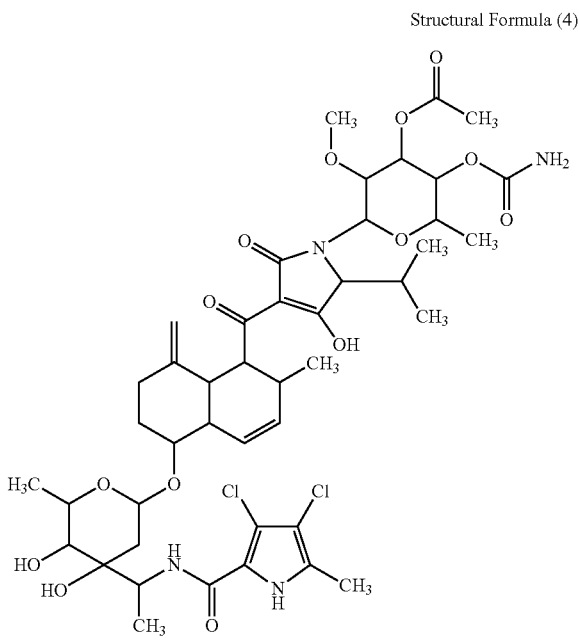 [SMILES: C=C1CCC(OC2CC(O)(C(C)NC(=O)c3[nH]c(C)c(Cl)c3Cl)C(O)C(C)O2)C2C=CC(C)C(C(=O)C3=C(O)C(C(C)C)N(C4OC(C)C(OC(N)=O)C(OC(C)=O)C4OC)C3=O)C12]

<Hydrolysis of Amycolamicin>

4M hydrochloric acid (1 mL) was mixed with a tetrahydrofuran solution (0.5 mL) of amycolamicin (2.05 mg, 2.18 nmol) and the resultant mixture was stirred at room temperature for 2 hours to perform hydrolysis. After the hydrolysis reaction had been terminated with 10 mL of a saturated sodium bicarbonate aqueous solution, the reaction mixture was extracted with ethyl acetate three times. The obtained organic layer was washed with saturated brine and dehydrated with magnesium sulfate. After the magnesium sulfate had been removed through filtration, the solvent was evaporated under reduced pressure. The residue was purified through thin-layer silica gel chromatography (developing solvent: ethyl acetate:methanol (90:10, by volume)) to thereby obtain compound 1 as a hydrolyzate. The yield amount of the compound 1 was found to be 0.78 mg where the mole yield was 97%.

Through analysis of the obtained compound 1 for physico-chemical properties, it was found to have the physico-chemical properties as shown below. From the physico-chemical properties, it was confirmed that the compound 1 was a new compound having a structure expressed by the following Structural Formula (1). Also, this compound 1 was found to have tautomerism.

(1) Appearance: colorless syrup
(2) Molecular formula: $C_{14}H_{20}Cl_2N_2O_5$
(3) High resolution mass spectrometry (HRESIMS: positive ion mode)
  Found: m/z 389.0640 (M+Na)⁺
  Calcd: m/z 389.0641 (as $C_{14}H_{20}Cl_2N_2O_5Na$)
(4) Specific rotation $[\alpha]_D^{23}$=+15° (c0.51, chloroform)
(5) Peaks of ¹H nuclear magnetic resonance spectra measured in deuterated chloroform at 30° C. and 600 MHz are as follows.
—α—Form of Compound 1—
  δpm:1.20(3H,d,J=6.9 Hz),1.20(3H,d,J=6.2 Hz),1.72(1H, dd,J=3.8,14.1 Hz),1.84(1H,dd,J=1.4,14.1 Hz),2.23(3H,s), 3.07(1H,d,J=9.2 Hz),3.16(1H,t,J=9.2 Hz,),3.88(1H,dq, J=9.2,6. 2 Hz),4.32(1H,pent.,J=7.2 Hz),4.97(1H,s),5.09(1H, dd,J=3.3,8.0 Hz),5.32(1H,d,J=9.0 Hz),6.74(1H,d,J=6.8 Hz), 10.20(1H,brs)
—β—Form of Compound 1—
  δpm:1.19(3H,d,J=6.2 Hz),1.20(3H,d,J=6.9 Hz),1.42(1H, dd,J=9.3,13.1 Hz),1.80(1H,dd,J=2.1,13.1 Hz),2.23(3H,s), 3.02(1H,d,J=8.9 Hz),3.11(1H,t,8.9 Hz,),3.58(1H,dq,J=8.9, 6.2 Hz),3.92(1H,s),4.24(1H,d,J=6.2 Hz),4.31(1H,pent., J=7.4 Hz),4.94(1H,ddd,J=2.1,6.2,9. 3 Hz),6.70(1H,d,J=6.6 Hz),10.20(1H,brs)
(6) Peaks of ¹³C nuclear magnetic resonance spectra measured in deuterated chloroform at 30° C. and 150 MHz are as follows.
—α—Form of compound 1—
  δpm:11.1(q),16.2(q),18.5(q),38.8(t),52.3(d),71.1(d),74.3 (d),76.3(s),92.7(d),110.3(s),111.5(s),119.8(s),129.7(s), 161.0(s)
—β—Form of Compound 1—
  δpm:11.1(q),16.2(q),18.6(q),34.8(t),52.3(d),65.1(d),74.5 (d),77.2(s),93.3(d),110.2(s),111.7(s),119.6(s),129.5(s), 161.2(s)

Structural Formula (1)

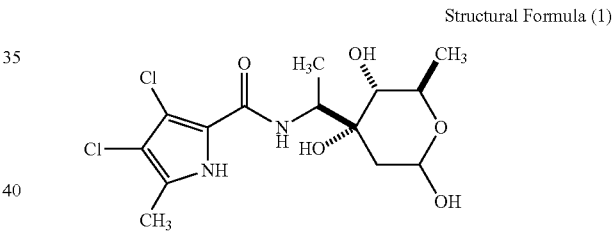

Example 2

Production of Compounds 2 and 3

5% by mass methanol solution of hydrogen chloride (1 mL) was mixed with a methanol solution (1 mL) of amycolamicin (19.5 mg, 20 7 nmol) and the resultant mixture was stirred at room temperature for 3 hours to perform solvolysis. After the solvolysis reaction had been terminated with 10 mL of a saturated sodium bicarbonate aqueous solution, the reaction mixture was extracted with ethyl acetate three times. The obtained organic layer was washed with saturated brine and dehydrated with magnesium sulfate. After the magnesium sulfate had been removed through filtration, the solvent was evaporated under reduced pressure. The residue was purified through thin-layer silica gel chromatography (developing solvent: ethyl acetate:methanol (95:5, by volume)) to thereby obtain β-methylglycoside compound (compound 2) and α-methylglycoside compound (compound 3). The yield amount of the compound 2 was found to be 4.8 mg where the mole yield was 64%. The yield amount of the compound 3 was found to be 2.5 mg where the mole yield was 33%.

Through analysis of the obtained compound 2 for physico-chemical properties, it was found to have the physico-chemical properties as shown below. From the physico-chemical properties, it was confirmed that the compound 2 was a new compound having a structure expressed by the following Structural Formula (2).

(1) Appearance: colorless syrup
(2) Molecular formula: $C_{15}H_{22}Cl_2N_2O_5$
(3) High resolution mass spectrometry (HRESIMS: positive ion mode)
  Found: m/z 403.0788 (M+Na)$^+$
  Calcd: m/z 403.0798 (as $C_{15}H_{22}Cl_2N_2O_5Na$)
(4) Specific rotation $[\alpha]_D^{23}=-113°$ (c0.24, chloroform)
(5) Peaks of $^1$H nuclear magnetic resonance spectra measured in deuterated chloroform at 30° C. and 600 MHz are as follows.
  δpm:1.30(3H,d,J=7.3 Hz),1.34(3H,d,J=6.2 Hz),1.49(1H,dd,J=9.3,13.1 Hz),1.92(1H,dd,J=2.1,13.1 Hz),2.28(3H,s),2.50(1H,brs),3.17(1H,brt,J=7.9 Hz),3.48(3H,s),3.64(1H,dq,J=9.3,6.2, Hz),4.42(1H,dq,J=7.3,6.2 Hz),4.69(1H,dd,J=2.1,9.3 Hz),5.22(1H,brs),6.63(1H,d,J=6.2 Hz),9.5-9.6(1H,brs)
(6) Peaks of $^{13}$C nuclear magnetic resonance spectra measured in deuterated chloroform at 30° C. and 150 MHz are as follows.
  δpm:11.4(q),16.1(q),18.0(q),36.3(t),52.6(d),55.6(q),70.4(d),74.2(s),76.2(d),99.7(d),111.1(s),112.4(s),117.4(s),128.7(s),161.3(s)

Structural Formula (2)

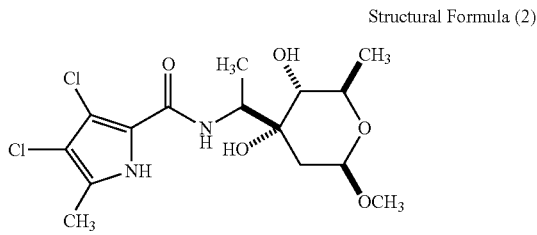 [SMILES: CO[C@H]1C[C@@](O)([C@H](C)NC(=O)c2[nH]c(C)c(Cl)c2Cl)[C@H](O)[C@@H](C)O1]

Through analysis of the obtained compound 3 for physico-chemical properties, it was found to have the physico-chemical properties as shown below. From the physico-chemical properties, it was confirmed that the compound 3 was a new compound having a structure expressed by the following Structural Formula (3).

(1) Appearance: colorless syrup
(2) Molecular formula: $C_{15}H_{22}Cl_2N_2O_5$
(3) High resolution mass spectrometry (HRESIMS: positive ion mode)
  Found: m/z 403.0788 (M+Na)$^+$
  Calcd: m/z 403.0798 (as $C_{15}H_{22}Cl_2N_2O_5Na$)
(4) Specific rotation $[\alpha]_D^{23}=+83°$ (c0.13, chloroform)
(5) Peaks of $^1$H nuclear magnetic resonance spectra measured in deuterated chloroform at 30° C. and 600 MHz are as follows.
  δpm:1.27(3H,d,J=6.8 Hz),1.33(3H,d,J=6.5 Hz),1.82(1H,dd,J=3.8,14.4 Hz),1.99(1H,dd,J=1.1,14.4 Hz),2.27(3H,s),2.30(1H,brs),3.24(1H,brd,J=9.4 Hz),3.38(3H,s),3.68(1H,dq,J=9.4,6.5, Hz),4.14(1H,brs),4.42(1H,dq,J=8.6,6.8 Hz),4.84(1H,brd,J=3.1 Hz),6.84(1H,d,J=8.6 Hz),9.74(1H,brs)
(6) Peaks of $^{13}$C nuclear magnetic resonance spectra measured in deuterated chloroform at 30° C. and 150 MHz are as follows.
  δpm:11.3(q),16.3(q),17.9(q),35.0(t),50.6(d),55.2(q),65.3(d),73.4(s),74.2(d),98.2(d),110.3(s),110.9(s),118.7(s),127.6(s),159.3(s)

Structural Formula (3)

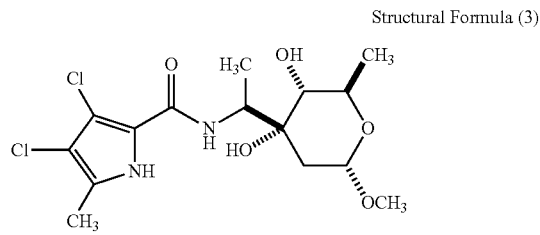 [SMILES: CO[C@@H]1C[C@@](O)([C@H](C)NC(=O)c2[nH]c(C)c(Cl)c2Cl)[C@H](O)[C@@H](C)O1]

Each of the obtained amycolose derivatives (compounds 1, 2 and 3) was measured for cell growth suppressive activity in Test Example 1 described below.

Test Example 1

Cell Growth Suppressive Activity)

Human prostate stromal cells PrSC (product of Bio Whittaker) were added to DMEM (product of NISSUI PHARMACEUTICAL CO., LTD.) containing 10% by mass FBS (fetal bovine serum) (product of ICN Biomedicals) to prepare a cell suspension having a concentration of 5×10$^4$ cells/mL. The cell suspension was placed in a 96-well plate in an amount of 0.1 mL per well. Each of the amycolose derivatives (compounds 1, 2 and 3) was added to the wells at a final concentration of 0.024 µg/mL, 0.098 µg/mL, 0.391 µg/mL, 1.563 µg/mL, 6.25 µg/mL, 25 µg/mL or 100 µg/mL, followed by culturing in an incubator for 3 days at 37° C. and 5% CO$_2$. Then, MTT (3-[4,5-dimethylthiazol-2-yl]-2,5-diphenyltetrazolium bromide) (product of Sigma Co.), which had been adjusted with a phosphate buffer to have a concentration of 5 mg/mL, was added to each well in an amount of 10 µL, followed by culturing in an incubator for 4 hours at 37° C. and 5% CO$_2$. Subsequently, 10 µL of 20% by mass SDS (sodium dodecylsulphate) prepared with 10 mM hydrochloric acid was added to each well, and the plate was left to stand still overnight at 37° C. to dissolve formazan formed from MTT. Thereafter, the plate was measured for absorbance at 570 nm with an absorptiometer (hereinafter may be referred to as "amycolose derivative-added sample's absorbance"). Regarding as 100% the absorbance measured when no amycolose derivative was added (hereinafter may be referred to as "control absorbance"), the cell growth rate in each of the amycolose derivatives (compounds 1, 2 and 3) at the above concentrations was calculated using the following equation (1). The results are shown in FIG. 5.

Cell growth rate (%)=amycolose derivative-added sample's absorbance/control absorbance×100     Equation (1)

Figure 5:
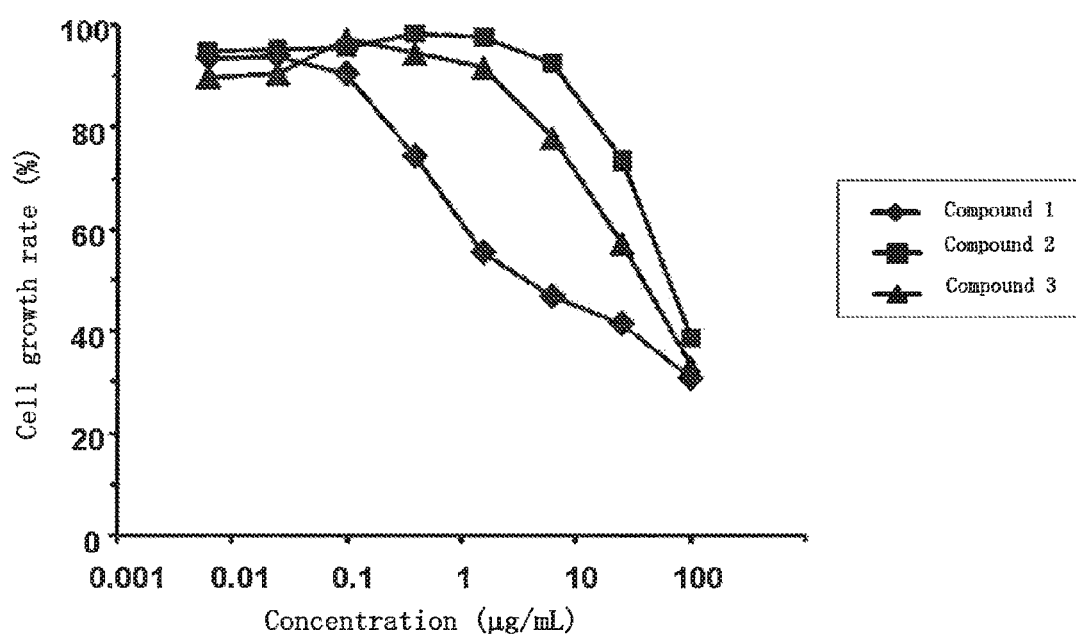
FIG. 5 is a graph of cell growth suppressive activities exhibited by amycolose derivatives (compounds 1, 2 and 3), where the vertical axis: cell growth rate (%) and the horizontal axis: concentrations of amycolose derivative (μg/mL).

As is clear from FIG. 5, the amycolose derivatives (compounds 1, 2 and 3) were found to exhibit cell growth suppressive activity. Among them, the compound 1 was found to exhibit a remarkable cell growth suppressive activity.

Embodiments of the present invention are as follows.

<1>A compound having a structure expressed by the following General Formula (1) or a salt thereof:

General Formula (1)

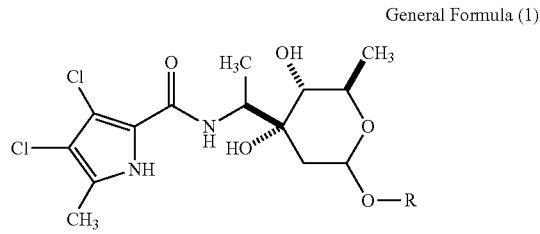

where "R" denotes a hydrogen atom or an alkyl group.

<2>The compound or the salt according to <1>, wherein the "R" is a hydrogen atom.

<3>The compound or the salt according to <1>, wherein the "R" is a methyl group.

<4>A method for producing a compound having a structure represented by the following General Formula (1) or a salt thereof, the method including:

culturing a microorganism belonging to the genus *Amycolatopsis* and capable of producing a compound having a structure expressed by the following Structural Formula (4) or a salt thereof;

isolating the compound having a structure expressed by the following Structural Formula (4) or the salt thereof from a culture obtained from the culturing; and decomposing the compound having a structure expressed by the following Structural Formula (4) or the salt thereof to produce a compound having a structure represented by the following General Formula (1) or a salt thereof:

General Formula (1)

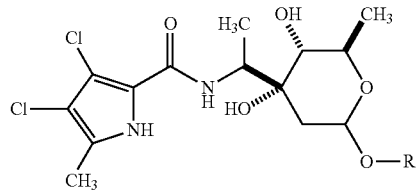

where "R" denotes a hydrogen atom or an alkyl group.

Structural Formula (4)

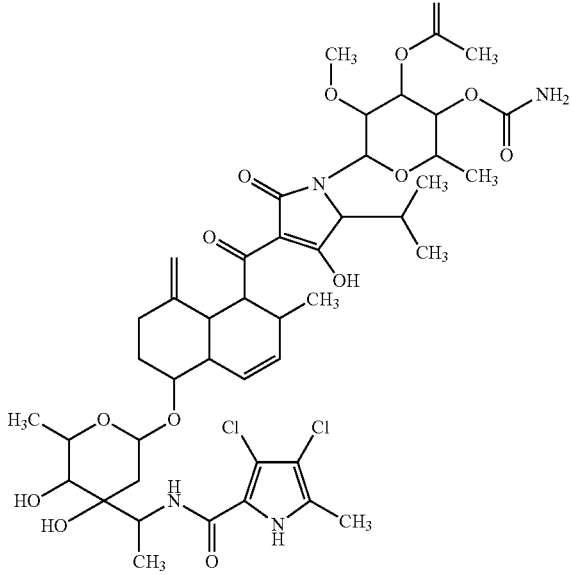

<5>The method according to <4>, wherein the decomposing is performed by hydrolysis with an acidic aqueous solution to produce a compound having a structure expressed by the following Structural Formula (1) or a salt thereof.

Structural Formula (1)

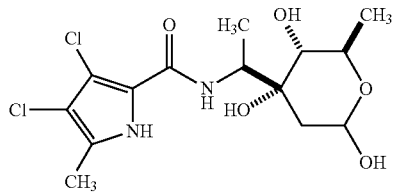

<6>The method according to <5>, wherein the acidic aqueous solution contains at least one selected from the group consisting of acetic acid, sulfuric acid, nitric acid and hydrogen chloride.

<7>The method according to <4>, wherein the decomposing is performed by solvolysis with an alcohol solution to produce a compound having a structure expressed by at least one of the following Structural Formulas (2) and (3) or a salt thereof.

Structural Formula (2)

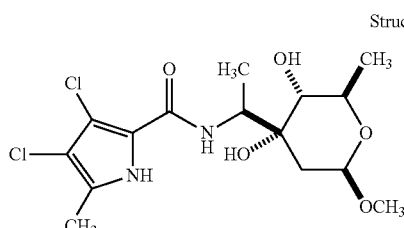

Structural Formula (3)

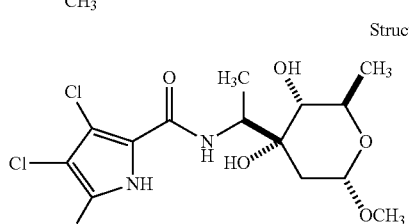

<8>The method according to <7>, wherein the alcohol solution is an acidic alcohol solution containing at least one selected from the group consisting of acetic acid, sulfuric acid, nitric acid and hydrogen chloride.

<9>The method according to any one of <4> to <8>, wherein the microorganism is a microorganism of *Amycolatopsis* sp. MK575-fF5 strain deposited under accession number FERM P-21465.

<10>A pharmaceutical composition including:

a compound represented by the following General Formula (1) or a salt thereof.

General Formula (1)

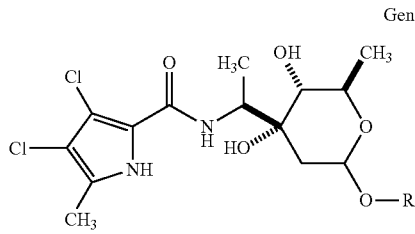

where "R" denotes a hydrogen atom or an alkyl group.

<11> The pharmaceutical composition according to <10>, wherein the pharmaceutical composition is a cell growth suppressive agent.

Industrial Applicability

The amycolose derivatives or salts thereof according to the present invention have an excellent cell growth suppressive activity and thus can suitably be used as an active ingredient of a pharmaceutical composition that suppresses the growth of cancer cells and other cells.

What is claimed is:

1. A compound having a structure expressed by the following General Formula (1) or a salt thereof:

General Formula (1)

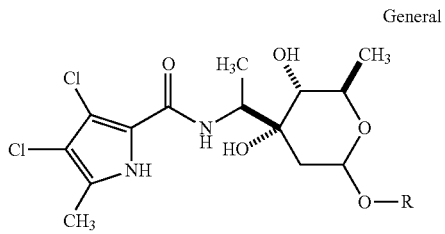

where "R" denotes a hydrogen atom or an alkyl group.

2. The compound or the salt according to claim 1, wherein the "R" is a hydrogen atom.

3. The compound or the salt according to claim 1, wherein the "R" is a methyl group.

4. A method for producing a compound having a structure represented by the following General Formula (1) or a salt thereof, the method comprising:

culturing a microorganism belonging to the genus *Amycolatopsis* and capable of producing a compound having a structure expressed by the following Structural Formula (4) or a salt thereof;

isolating the compound having a structure expressed by the following Structural Formula (4) or the salt thereof from a culture obtained from the culturing; and decomposing the compound having a structure expressed by the following Structural Formula (4) or the salt thereof to produce a compound having a structure represented by the following General Formula (1) or a salt thereof:

General Formula (1)

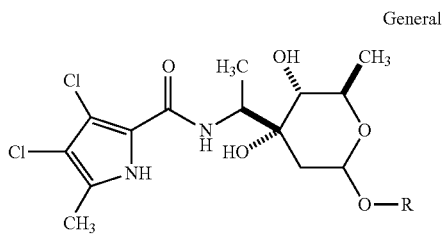

where "R" denotes a hydrogen atom or an alkyl group

Structural Formula (4)

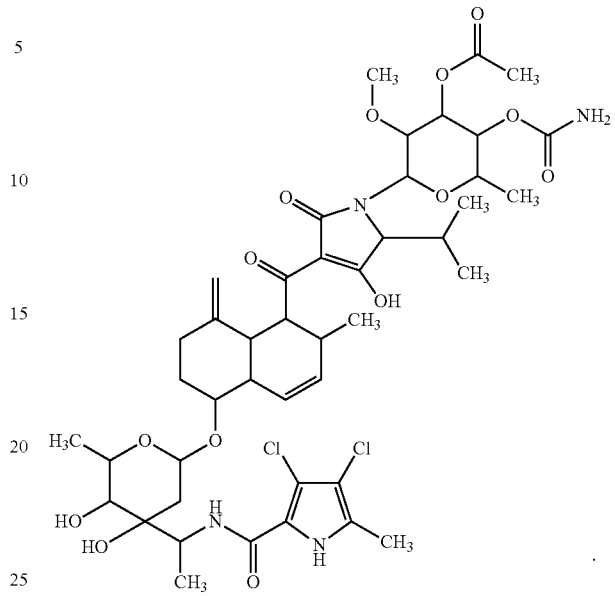

5. The method according to claim 4, wherein the decomposing is performed by hydrolysis with an acidic aqueous solution to produce a compound having a structure expressed by the following Structural Formula (1) or a salt thereof Structural Formula (1)

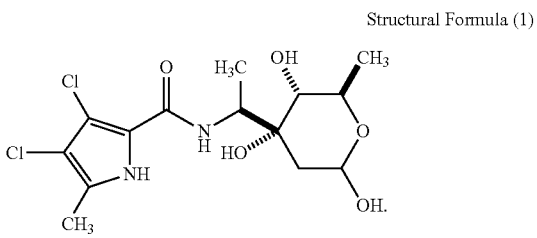

6. The method according to claim 5, wherein the acidic aqueous solution contains at least one selected from the group consisting of acetic acid, sulfuric acid, nitric acid and hydrogen chloride.

7. The method according to claim 4, wherein the decomposing is performed by solvolysis with an alcohol solution to produce a compound having a structure expressed by at least one of the following Structural Formulas (2) and (3) or a salt thereof Structural Formula (2)

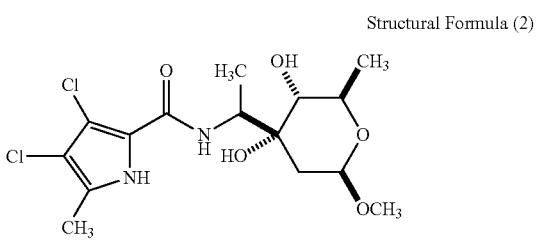

-continued

Structural Formula (3)

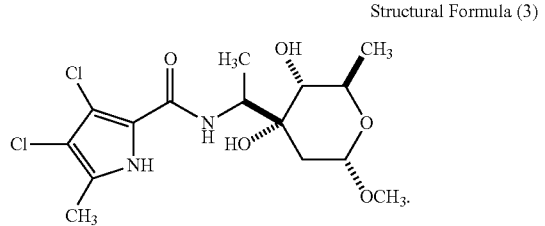

8. The method according to claim 7, wherein the alcohol solution is an acidic alcohol solution containing at least one selected from the group consisting of acetic acid, sulfuric acid, nitric acid and hydrogen chloride.

9. A pharmaceutical composition comprising:
a compound represented by the following General Formula (1) or a salt thereof:

General Formula (1)

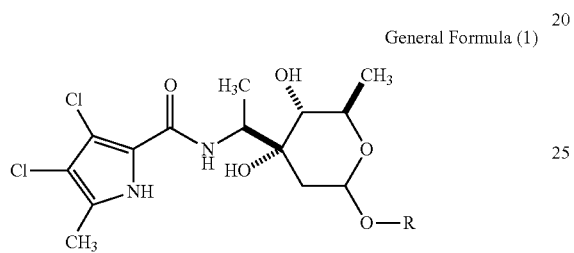

where "R" denotes a hydrogen atom or an alkyl group.

* * * * *